(12) United States Patent
Wesley et al.

(10) Patent No.: US 6,342,259 B1
(45) Date of Patent: Jan. 29, 2002

(54) MONITORING OF DOUGH PROPERTIES

(75) Inventors: Ian John Wesley, Ryde NSW (AU); Nigel Grant Larsen, St. Albans Christchurch (NZ); Brian George Osborne, Cowan NSW; John Howard Skerritt, Cook ACT, both of (AU)

(73) Assignees: Grains Research and Development Corporation, Barton ACT; Commonwealth Scientific and Industrial Research Organisation, Campbell ACT, both of (AU); New Zealand Institute for Crop and Food Limited, Lincoln (NZ); BRI Australia Limited, North Ryde (AU)

( * ) Notice: Subject to any disclaimer, the term of this patent is extended or adjusted under 35 U.S.C. 154(b) by 0 days.

(21) Appl. No.: 09/403,279
(22) PCT Filed: Apr. 16, 1998
(86) PCT No.: PCT/AU98/00267
§ 371 Date: Dec. 20, 1999
§ 102(e) Date: Dec. 20, 1999
(87) PCT Pub. No.: WO98/48271
PCT Pub. Date: Oct. 29, 1998

(30) Foreign Application Priority Data

Apr. 18, 1997 (AU) .............................. PO 6303

(51) Int. Cl.⁷ .................... G01N 33/10; G01N 21/35
(52) U.S. Cl. ........................................................ 426/231
(58) Field of Search ............................. 426/231, 234, 426/248, 504

(56) References Cited

U.S. PATENT DOCUMENTS 5,258,825 A  * 11/1993  Reed et al. .................. 356/402
5,319,200 A    6/1994  Rosenthal et al. .......... 250/341
5,668,374 A    9/1997  DiFoggio et al. ....... 250/339.12

FOREIGN PATENT DOCUMENTS

| EP | 0 511 184 | 10/1992 |
| WO | 81/00775 | 3/1981 |
| WO | 94/12866 | 6/1994 |

OTHER PUBLICATIONS

Derwent Abstract Accession No. 91–248140/94, Class S03, JP 31–60345 A (Satake Seisakusho) Jul. 10, 1991.
Derwent Abstract Accession No. 92–004927/01, Class S03, JP 32–59732 A (Satake Seisakusho) Nov. 19, 1991.
Goulden, "Diffuse Reflexion Spectra Of Dairy Products In The Near Infra–Red Region", *The Journal of Dairy Research*, vol. 24(2):242–251, (Dec. 1957).
Fateley et al., "Recognizing The Validity Of Prior Art: Recent Patents Involving Electromagnetic Radiation", (Jan. 1999).
Funk et al., "ARS Perten Meeting", (Jan. 1997) 2 pages.
Dowell et al., "Automated Single Wheat Kernel Quality Measurement Using Near–Infrared Reflectance", pp. 1–9, (Jan. 1997).
Wang et al., "Single Wheat Kernel Color Classification By Using Near–Infrared Reflectance Spectra", *Cereal Chemistry*, vol. 76(1):30–33, (Jan. 1999).
Wang et al., "Single Wheat Kernel Size Effects On Near–Infrared Reflectance Spectra and Color Classification", *Cereal Chemistry*, Vo. 76(1):34–37, (Jan. 1999).

(List continued on next page.)

*Primary Examiner*—Keith Hendricks
(74) *Attorney, Agent, or Firm*—Foley & Lardner

(57) ABSTRACT

The present invention relates to a rapid and non-evasive method of monitoring dough development and dough mixing properties using near infrared (NIR) spectroscopy. In particular, the present invention relates to a method of measuring the change in constituents of a grain flour dough during mixing.

7 Claims, 6 Drawing Sheets

OTHER PUBLICATIONS

Wang et al., "Predicting The Number Of Diminant R Alleles In Single Wheat Kernels Using Visible And Near–Infrared Reflectance Spectra", *Cereal Chemistry*, vol. 76(1):6–8, (Jan. 1999).

Dowell, "Automated Color Classification Of Single Wheat Kernels Using Visible And Near–Infrared Reflectance", *Cereal Chemistry*, vol. 75(1):142–144 (Jan. 1999).

Dowell et al., "Detection Of Scab In Single Wheat Kernels Using NIR Spectroscopy", pp. 1–11, (Jan. 1998).

Dowell, "Automated Color Classification Of Single Wheat Kernels Using Visible And Near–Infrared Reflectance", *Cereal Chemistry*, vol. 75(1):42–144, (Jan. 1998).

Wang et al., "Single Wheat Kernel Color Classification Using Neural Networks", *Transactions of the ASAE*, vol. 42(1):233–240, (Jan. 1999).

Dowell, "Effect of NaOH On Visible Wavelength Spectra Of Single Wheat Kernels And Color Classification Efficiency", *Cereal Chemistry*, vol. 74(5):617–620, (May 1997).

Archibald et al., "Development Of Short Wavelength Near–Infrared Spectral Imaging For Grain Color Classification"(Date N.A.).

Dowell et al., "Automated Nondestructive Detection Of Internal Insect Infestation Of Wheat Kernels By Using Near–Infrared Reflectance Spectroscopy", *Journal of Economic Entomology*, vol. 91(4):899–904, (Apr. 1998).

P.W. Voisey et al., "An electronic recording dough mixer", Cereal Chemistry, vol. 43, Jan. 1966, pp. 408–419.

P.W. Voisey et al., "An Electronic Recording Grain Research Laboratory Mixer", Cereal Chemistry, vol. 51(5) May 1974, pp. 841–847.

R.A. Anderson et al., "Recording Apparatus for Measuring Some Mixing Characteristics of Flour–Water Batters", Cereal Chemistry, vol. 34, Jan. 1967, pp. 379–388.

R.H. Kilborn et al., "Power–Input Meter for Laboratory Dough Mixers", Cereal Chemistry, vol. 42, pp. 432–435, Jan. 1965.

R.H. Kilborn et al., "Device Senses Changes in Dough Consistency During Dough Mixing", Bakers Journal, Jan. 1981, pp. 16–19.

A.J. Wilson et al., "Dough probe investigation", Science Report, Food Technology in New Zealand, vol. 30, Jan. 1995, pp. 36–40.

S. Zounis et al, "Predicting Test Bakery Requirements from Laboratory Mixing Tests", J. of Cereal Science, vol. 25, Jan. 1997, pp. 185–196.

K.R. Preson et al., "Effects of Acid–Soluble and Acid–Insoluble Gluten Proteins on the Rheological and Baking Properties of Wheat Flours", Cereal Chemistry, vol. 57, No. 5, May 1980, pp. 314–320.

F. MacRitchie, Studies of the Methodology for Fractionation and Reconstitution of Wheat Flours, J. of Cereal Science, vol. 3, Mar. 1985, pp. 221–230.

F. MacRitchie, "Physicochemical Processing in Mixing", Royal Society of Chemistry, London, Jan. 1986, pp. 132–146.

B.G. Osborne et al., "Application of Near Infrared Reflectance . . . Analysis of Biscuits and Biscuit Doughs", J. Sci. Food Agric., vol. 35, Jan. 1984, pp. 99–105.

R.H. Wilson et al., "Comparison of Fourier Transform Mid Infrared Spectroscopy . . . Staling of Bread", J. Sci. Agric, vol. 54, Jan. 1991, pp. 471–483.

\* cited by examiner

MONITORING OF DOUGH PROPERTIES

This application is a 371 of PCT/AU98/00267, filed Apr. 16, 1999.

The present invention relates to a novel, rapid and non-invasive method of monitoring the redistribution of water in protein-containing multi-phase systems during a mixing or processing step. The method of the invention is particularly applicable to food products. In a preferred embodiment, the invention relates to monitoring dough development and dough mixing properties using near infrared (NIR) spectroscopy, particularly through monitoring the variation in three specific absorbance wavelengths.

BACKGROUND OF THE INVENTION

Dough mixing is the most critical stage in the production of bread products. The dough must be mixed to a stage loosely referred to as "optimum development", and water must be added to the optimum absorption level of the flour for subsequent ease of processing and to ensure good end-product quality. The characteristics of the dough are partly affected by the type of flour used, for example "very strong flour", "strong flour", "medium flour" or "biscuit flour". "Very strong" or "strong" flours are characterised by their rheological "strength" properties as having a high degree of resistance to extension when a dough prepared from the flour is stretched using a standard testing device known as a Brabender Extensograph. They also have a long dough mixing or development time when mixed in either a commercial dough mixer or in one of the smaller test mixers, for example the Mixograph or the Farinograph. The dough also has a high degree of "stability" or resistance to breakdown. Thus if mixed for a longer period than the optimum mixing time, such a dough will retain its characteristic mixing properties. Doughs which do not have strength breakdown, so that they have a sloppy, batter-like consistency, and can be mixed with little resistance. A dough which is prone to breakdown will cause enormous problems during processing. For example such a dough will not hold the gas produced by the yeast during baking, and thus will not rise so as to provide a good bread loaf volume and consistency. Conversely, a "medium" strength flour will exhibit lower stability and have a higher degree of breakdown, while a "biscuit" flour would be unsuitable for bread-making because of its poor stability. Stability is not required for biscuits. For these reasons, monitoring of dough development is of enormous importance to the baking industry.

A number of methods are commonly used to estimate dough development using laboratory scale mixers. The most popular measurement is that of mixing torque (Voisey, P. W., Miller, H. and Kloek, M., Cereal Chemistry, 1966 43 408–419; Voisey, P. W. Cereal Chemistry, 1974 51 841–847), using strain gauges attached to the mixer. An alternative method involves the measurement of the power consumption of the mixer (Anderson, R. A. and Lancaster, E. B. Cereal Chemistry, 1967 34 379–388; Kilborn, R. H. and Dempster, C. J. Cereal Chemistry, 1965 42 432–435). Alternatively, dough development in commercial mixers can be measured using a probe that, through a load cell, measures the force exerted by dough moving around the mixing bowl (Kilborn, R. H and Preston, K. R., Bakers Journal, 1981 16–19; Wilson, A. J. and Newberry, M. P., Food Technology in New Zealand, 1995 30 36–40). Each of these measurements, whilst useful, requires or is based on the results of direct physical interaction with the dough, and does not directly measure the chemical changes that occur during dough development. In addition, it has been reported that mixing beyond the time to peak resistance, as indicated by power consumption and mixograph produces higher quality loaves of bread (Zounis, S. and Quail, K. J., "Predicting Test Bakery Requirements from Laboratory Mixing Tests", Journal of Cereal Science, 1997 25 185–196).

It is also well established that there is a relationship between glutenin content (or glutenin/gliadin ratio) and particular dough properties. See for example, Preston, K. R. and Tipples, K. H., Cereal Chemistry, 1980 57 314–320; MacRitchie, F., Journal of Cereal Science, 1985 3 221–230; and MacRitchie, F., Royal Society of Chemistry, London, 1986 132–146. During mixing, changes can occur in the composition of the polymeric phase of the gluten which relate to the dough rheological properties.

As used in this specification the term "dough" refers to milled flour or wholemeal from a cereal, including but not limited to bread wheat (*Triticum aestivum* L.), added to water and other ingredients in any proportion which may include but are not limited to yeast, fat, salt and other Generally Recognized as Safe (GRAS) food ingredients, to which mechanical work is applied to develop a product useful for food application.

As used in this specification the term "gliadin protein" is applied to a family of glutamine- and proline-rich proteins of wheat seed endosperm, which proteins are monomeric seed storage compounds and which subunits are encoded by genes on the short arms of homologous chromosomes 1 and 6 of wheat (*Triticum aestivum, Triticum turgidum* var. durum) and related cereal species. As used in this specification the term "glutenin protein" is applied to a family of glutamine and proline-rich proteins of wheat seed endosperm, which proteins are a polymeric complex of disulfide-bonded seed storage polypeptide compounds and which subunits are encoded by genes on the long and short arms of homologous chromosomes 1 of wheat (*Triticum aestivum, Triticum turgidum* var. durum) and related cereal species.

The near infrared spectrum of flour consists of absorbances which are repeated at intervals across the wavelength range 800–2500 nm. The absorbances are due to specific chemical bonds and can be readily related to specific constituents of the flour.

NIR analysis has been used to monitor the principal constituents of flour, and to monitor water content of baked or processed foods through determination of specific absorbances in the near-infrared spectrum. It has been reported that NIR can be used to monitor the sucrose, fat, flour and water content of biscuit doughs (Osborne, B. G., Fearn, T., Miller, A. R. and Douglas, S., Journal of the Science of Food and Agriculture, 1984 35 99–105). NIR is most commonly used as a rapid analysis technique for quality control purposes, and usually involves calibration against a reference laboratory method. There are few studies on the use of NIR as a fundamental measurement tool, and even fewer on the use of NIR to follow chemical changes in materials. NIR has been used to follow the staling of bread (Wilson, R. H., Goodfellow, B. J., Belton, P. S., Osborne, B. G., Oliver, G. and Russell, P. L., J. Sci. Food. Agric. 1991 54 471–483) by fitting first order equations to spectral changes, and hence calculating rate constants for the staling process. On the basis of these results, the authors concluded that NIR could be used to gain information on the fundamental nature of the process that occurred during bread staling. However, the use of NIR to study the consistency of doughs has not been suggested.

Instruments and methods for determination of total protein content in dough or in whole grain have been described. U.S. Pat. No. 4,734,584 by Rosenthal discloses a NIR instrument for either reflectance or transmittance spectroscopy, depending on the sample chamber used, and with a range of wavelengths available for either mode. European Patent Application No. 511184 by Perten describes an instrument for very rapid NIR analysis of unground grain by reflectance spectroscopy, using a set of predetermined wavelengths in the range 1050–1400 nm provided by means of a continuous rotatable disc filter device. U.S. Pat. No. 5,258,825 by Reed and Psotka describes an apparatus for simultaneous visible and NIR analysis in a flour product, for determination of ash content and protein content respectively. The instrument may be used in either the reflectance or transmittance mode, and the preferred infrared wavelength is 1368 nm.

All of the instruments and methods described in the prior art are directed at measurement of protein content in wheat or other grains; protein content is loosely correlated with baking quality.

Not all of the wavelengths which are monitored in the near infrared reflectance spectrum (700–2500 nm) systematically vary in their intensities as a dough is processed. We have now found that the variation in absorbances at wavelengths in the second derivative spectrum (1160 nm (band of 1150–1170 nm)), 1200 (1190–1210 nm) and 1430 nm (band of 1420–1440 nm)) as the dough is mixed follows the same trend as mixer power consumption, and thus provides an estimate of dough development and breakdown.

The 1160 nm absorbance is the stretch-bend combination band of water, which is highly sensitive to the local environment of the water molecules, whilst the 1200 nm absorbance, which is a C—H stretch second overtone, is thought to be due predominantly to protein. The 1430 nm absorbance is a mixture of two absorbances, due to water and protein. We have found that all three bands show a reduction in peak area as dough mixing progresses, reaching a minimum at optimum dough development, and an increase as the dough mixing continues past peak mixer power consumption. In the case of the 1160 nm water absorbance, this is thought to be due to the binding and subsequent release of water as dough development proceeds through optimum. Consistent results were obtained for unyeasted and full formula doughs made from four flours of different strengths using two different laboratory mixers.

These findings form the basis of a non-invasive and very rapid method of analysis of multi-phase protein-containing systems, especially dough, grain or grain products. For dough, the results are available as the dough is mixed. The method can be used to differentiate the flours on the basis of the difference in mixing time and stability, and shows the potential of the technique for providing information on the chemical processes that occur during dough development.

We have now also found that glutenin and gliadin differ in the second derivative spectrum: glutenin has an absorbance minimum at 2350 nm (band of 2346–2354 nm), whereas gliadin has an absorbance minimum at 2340 nm (2336–2344 nm), an absorbance minimum at 2310 nm (2300–2320 nm), and an absorbance maximum at 2195 nm (2190–2200 nm).

We have obtained clear evidence that the gliadin and glutenin fractions from flours of diverse genotypes consistently differ in specific spectral characteristics. Specific spectral differences have consistently been observed between gliadin and glutenin in isolates from five wheat varieties and a commercial flour, and consistent results have been obtained. These features (or their repeat absorbances) can be used to follow the changes that occur in the glutenin and gliadin content as dough is mixed.

SUMMARY OF THE INVENTION

In a first aspect, the invention provides a method of monitoring a processing step in a protein and water-containing multi-phase system, comprising the step of analysing said protein and water-containing system by near infrared spectroscopy. Preferably the multi-phase system is a food product.

In a further aspect, the present invention provides a method of monitoring dough development and breakdown during mixing and other processing, comprising the step of analysing the dough by near infrared (NIR) spectroscopy.

In a preferred embodiment there is provided a method for analysis of the time of development of optimal dough consistency for bread manufacture comprising the step of using near infrared reflectance spectrometry to measure absorbance at 1160 nm, 1200 nm and 1430 nm.

Preferably the following spectral differences of glutenin from gliadin in the second derivative spectrum are also analysed: an absorbance minimum for glutenin at 2350 nm (2346–2354 nm), whereas gliadin has an absorbance minimum at 2340 nm (2336–2344 nm); an absorbance minimum at 2310 nm (2300–2320 nm), and an absorbance maximum at 2195 nm (2190–2200 nm).

Preferably the NIR spectroscopic method utilises fast diode array detection, such that spectra can be recorded in under 10 seconds, more preferably under 1 second, thus providing improved monitoring of doughs as they are mixed.

Preferably the method monitors a plurality of specific absorbances that exhibit a change in peak area as dough mixing progresses, reaching a minimum or maximum at optimum dough development, and a change in the opposite direction as the dough mixing continues past peak mixer power consumption.

In another aspect, the invention provides a method for the monitoring of glutenin and gliadin in a dough or other product derived from grain, comprising the step of using NIR spectroscopy to measure spectral differences of glutenin and gliadin in the second derivative spectrum, namely for glutenin an absorbance minimum at 2350 nm (2346–2354 nm) and for gliadin an absorbance minimum at 2340 nm (2336–2344 nm), an absorbance minimum at 2310 nm (2300–2320 nm) and an absorbance maximum at 2195 nm (2190–2200 nm) or the overtones thereof.

Optionally other stretch and or bend fundamental, combination or overtone bands of water and/or other fundamental, combination or overtone bands due to the C—H bonds in protein or lipid are also measured.

In a third aspect of the invention there is provided a method for predicting the change in glutenin and gliadin content in grain, wholemeal, flour, and dough, or is another product derived from said grain as described above.

It will be clearly understood that while the invention is described in detail for bakery products, particularly bread, the invention is equally applicable to other food and non-food multi-phase systems that involve the redistribution of water during a mixing or similar processing step. The person skilled in the art will readily be able to adapt the methods described herein for dough to other systems, using routine trial and error experimentation.

According to a fourth aspect, the invention provides an apparatus for NIR spectroscopic analysis of a grain, wholemeal, flour, dough, or is another product derived from said grain, comprising:

a) a source of near-infrared radiation;
b) a means for detection said near-infrared radiation; and
c) means whereby the dough or other product is exposed to said rear-infrared radiation source in appropriate relation to the detection means,
wherein either the source or detector is specific for the desired near-infrared radiation wavelength.

For analysis of dough according to the invention either the source or the detector is specific for wavelengths of 1160, 1200 and 1430 nm.

For determining relative proportions of glutenin and gliadin in a dough, the wavelengths will be those of the absorbance maxima and minima in the second derivative spectrum, as defined above, ie. 2530 nm, 2340 nm, 2310 nm and 2195 nm or their repeats.

The means c) for exposure of the sample to be analyzed to the source will depend on the nature of the sample, and the person skilled in the art will readily appreciate suitable devices. For example, a spectrometer may be positioned over a dough mixing vessel such that the dough surface is at the focal point of the source and detector.

Two principal types of detector are suitable for use in the apparatus of the invention. Most advantageously a diode array detector is used, since this enables a very large number of wavelengths to be measured virtually simultaneously, thus enabling the rapid measurement desirable in monitoring a fast process such as dough mixing. Alternatively a simple fixed filter device using transmission filters suitable for the desired wavelengths, and one or more additional filters to correct the spectra for the effects of scatter may be used. Diode array detectors are more expensive than filter instruments, although with improved technology the cost is becoming cheaper all the time. Fixed filter devices are slower but cheaper; they may be more suitable for certain applications.

In a number of the different aspects of the invention either reflectance NIR spectroscopy or transmittance NIR spectroscopy may be used. For transmittance spectroscopy a transmission probe is necessary, and suitable on-line probes are available for use in process monitoring applications. Reflectance spectroscopy is preferred for analysis of dough, as this is completely non-invasive and can be performed using a reflectance or interactance probe, or using the instrumentation alone. The person skilled in the art will readily be able to test which mode is most suitable for a given purpose.

The method of the present invention can be directly applied to equipment for the monitoring of optimal dough processing, and for the objective prediction of dough properties through NIR analysis of grain, wholemeal, flour or wheat products.

While the invention is described in detail in relation to wheat flour doughs, it will be clearly understood that the invention is also applicable to any cereal, grain or grain product derived from any grain in which glutenin and gliadin are present, including but not limited to mixed-grain doughs comprising rye, oats, barley and/or maize.

DETAILED DESCRIPTION OF THE INVENTION

Hereinafter given by way of non-limiting examples are preferred embodiments of the invention, describing the preparation of the dough and the measurement of the near-infrared reflectance characteristics of the dough during dough mixing and processing according to the present invention, and the use of the absorbances at the specific wavelengths to determine the optimal stage of dough processing.

EXAMPLE 1

Analysis of Dough Mixing Using a Monochromator NIR Instrument and a Fibre Optic Reflectance Probe A test mix of dough was made using 100 g flour in a small 6-pin mixer (National Manufacturing Company, Lincoln, Neb., USA). The dough was assessed by an experienced baker, and the water content adjusted to achieve a good quality dough. The standard recipe consisted of 100 parts flour, 2 parts salt, 2 parts fat and 1 part bread improver (65KSB malt flour, 100 ppm ascorbic acid).

Figure 1:
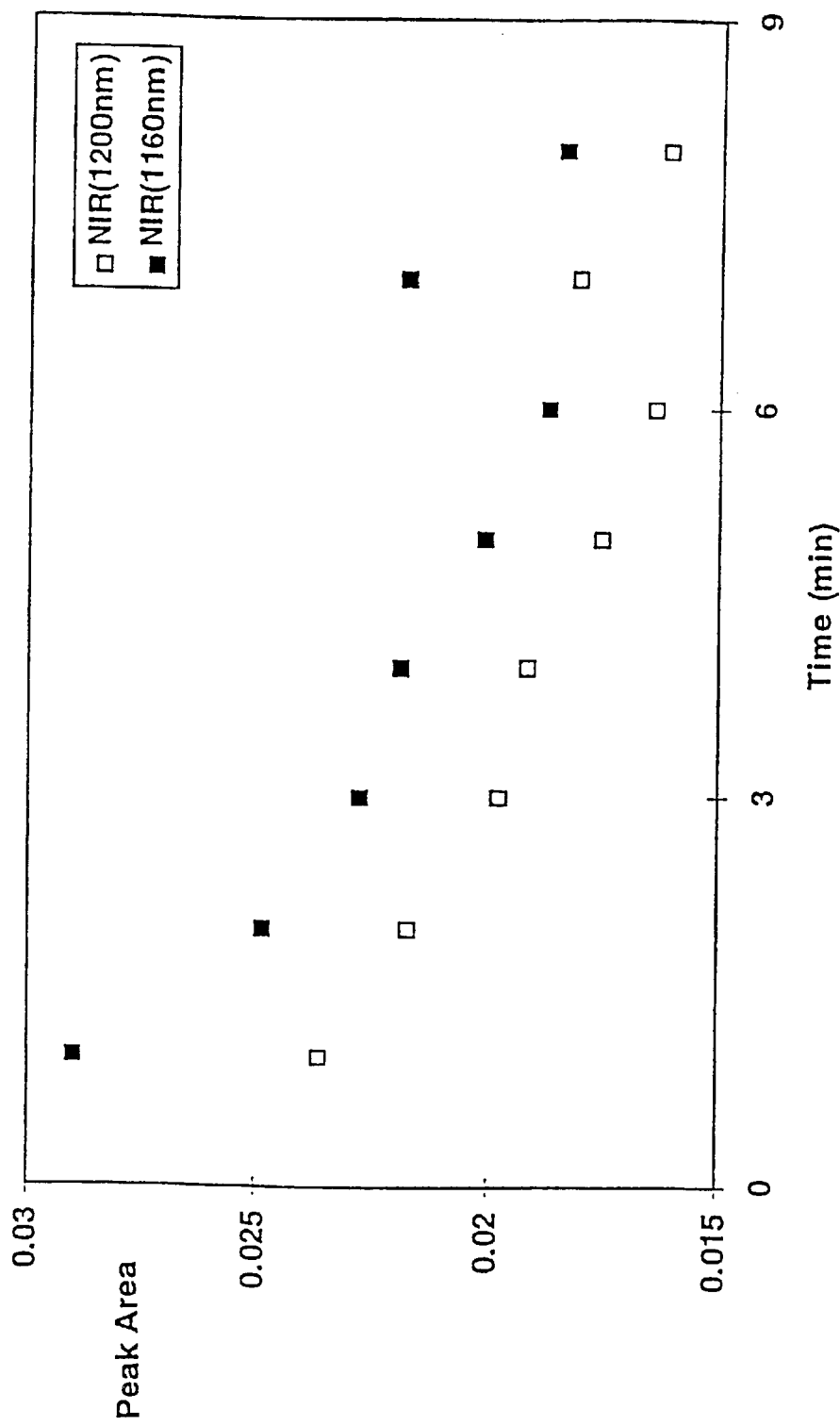
FIG. 1 shows the variation in peak area in the inverted 2nd derivative spectrum recorded on a NIRSystems 6500 with fibre optic probe for doughs mixed for different time periods using a 6-pin mixer.

Experiments were performed using a NIRSystems 6500 spectrometer fitted with a fibre optic reflectance probe (NIRSystems, Silver Spring, Md., USA) and a 6-pin mixer. Whilst this monochromator NIR instrument itself records the full NIR spectrum (1100–2500 nm) in this configuration, the transmission characteristics of the fibre optic probe are such that data in the region 2000–2500 nm is not useable. Experiments using the NIRSystems 6500 and fibre optic probe showed that there was a systematic variation in the peak areas of the peaks at 1160. This variation was identified as being due to water (Curcio, J. A. and Petty, C. C., "The near infrared absorption spectrum of liquid water", Journal of the Optical Society of America, 1951 41 302–304) and 1200 nm (due to C—$H_x$) (Law, D. P. and Tkatchuk, Cereal Chemistry, 1977 54 256–265). This is summarized in FIG. 1.

The absorbance at 1160 nm is an O—H stretch-bend combination band, and as such is considerably weaker than the first overtone absorption at 1450 nm. However, the first overtone is overlaid with absorbances due to the N—H first overtone and the first overtone of the C—H combination bands, and is therefore much more difficult to analyse. For this reason, it was decided to use the absorbance at 1160 nm.

EXAMPLE 2

Monitoring of Dough Mixing Using a Diode Array Spectrometer/Spiral Mixer

Four flours (a very strong flour, a strong flour, a medium strength flour and a biscuit flour) were obtained from Goodman Fielder Mills, Summer Hill, NSW, Australia. The properties of these flours are summarized in Table 1.

TABLE 1

Properties of Flours Used

| Sample | Very Strong Flour | Strong Flour | Medium Flour | Biscuit Flour |
|---|---|---|---|---|
| Protein (N × 5.7) % | 12.7 | 11.0 | 8.6 | 8.2 |
| Moisture % | 13.8 | 13.3 | 13.5 | 13.1 |
| Colour Grade (KJM Series 4 Colour Grader) | 1.3 | 0.6 | −0.8 | 0.3 |
| Starch Damage (AACC method 76-30A) | 6.3 | 7.1 | 6.2 | 5.1 |
| Brabender Farinograph Water Absorption | 66.3 | 63.5 | 59.6 | 56.7 |
| Brabender Farinograph Development Time | 6.5 | 5.0 | 1.5 | 1.5 |
| Brabender Farinograph Stability | 3.0 | 1.5 | 1.0 | 2.0 |
| Brabender Farinograph dough Weakening | 20 | 25 | 40 | 60 |
| Extensograph (45 min) Extensibility (cm) | 20.0 | 20.8 | 17.8 | 16.5 |
| Extensograph (45 min) Resistance (BU) | 414 | 320 | 250 | 160 |
| Optimum water absorption (parts per 100 parts flour) | 61 | 60 | 60 | 67 |

Doughs were mixed using different mixers, such as a 5 kg Spiral Mixer (Eberhardt Gmbh, Munich, Germany) using 4 kg of flour per mix. The Eberhardt mixer spiral rotates at 224 rpm and the bowl rotates at 28 rpm when operating under no-load conditions. A standard recipe for the dry ingredients was used, and the water content adjusted for each flour. This was achieved by making a test mix using 100 g flour in a small 6-pin mixer (National Manufacturing Company, Lincoln, Nebr., USA). The dough was assessed by an experienced baker and the water content adjusted to achieve a good quality dough. The standard recipe consisted of 100 parts flour, 2 parts salt, 2 parts fat and 1 part bread improver (65 KSB malt flour, 100 ppm ascorbic acid). Full formula doughs were also mixed using the Very Strong Flour and 2.5 parts compressed yeast (Mauri Foods, Camellia, NSW, Australia). Power consumption curves were recorded for each mix using the Easymix system (BRI Australia Ltd, North Ryde, Australia). Easymix records the power consumption (in watts) of the mixer as the dough is mixed, and the peak power consumption is the point of maximum dough resistance, which is closely related to the optimum mixing point of the dough for baking purposes.

The Perten DA-7000 diode array NIR spectrometer (Perten Instruments, Springfield, Ill., USA) offered a more flexible method of recording spectral data. This instrument operates over the range 400–1700 nm, recording Log(1/R) values at 5 nm intervals. Data acquisition is fast. Typically, 30 scans are recorded per second and internally averaged to give 1 spectrum. The instrument is of an open design, having no sample compartment. Instead the user places the sample on a tray located at the focal point of the light source of the instrument. Illumination of the sample and detection of the scattered radiation is from below. In our experiments, the sample tray was removed and the instrument inverted. A support frame was designed which allowed the instrument to be placed over the mixing bowl of a dough mixer, with the dough at the approximate focal point of the instrument. A software program was written to collect data at specified time intervals. The fastest sampling rate achieved was 1 spectrum every 2 seconds.

The spectra were processed and the data analysed using GRAMS/32 spectral software (Galactic Industries Corporation, Salem, N.H., USA). Firstly, the second derivative of each spectrum was calculated using a 4 point (20 nm) gap. A 4-point binomial smoothing function was then applied to the derivatised spectrum, and the resulting spectrum inverted (ie. multiplied by −1) before peak areas were measured. The use of the second derivative spectrum has a number of advantages. Baseline shifts between spectra, caused by the position of the dough in the mixer, are largely removed and overlapping absorbances are separated, making analysis easier. Inverting the spectrum made using the GRAMS/32 program to measure the peak areas easier. The peak area data could then be plotted against mixing time for each peak in the second derivative spectrum.

Figure 2:
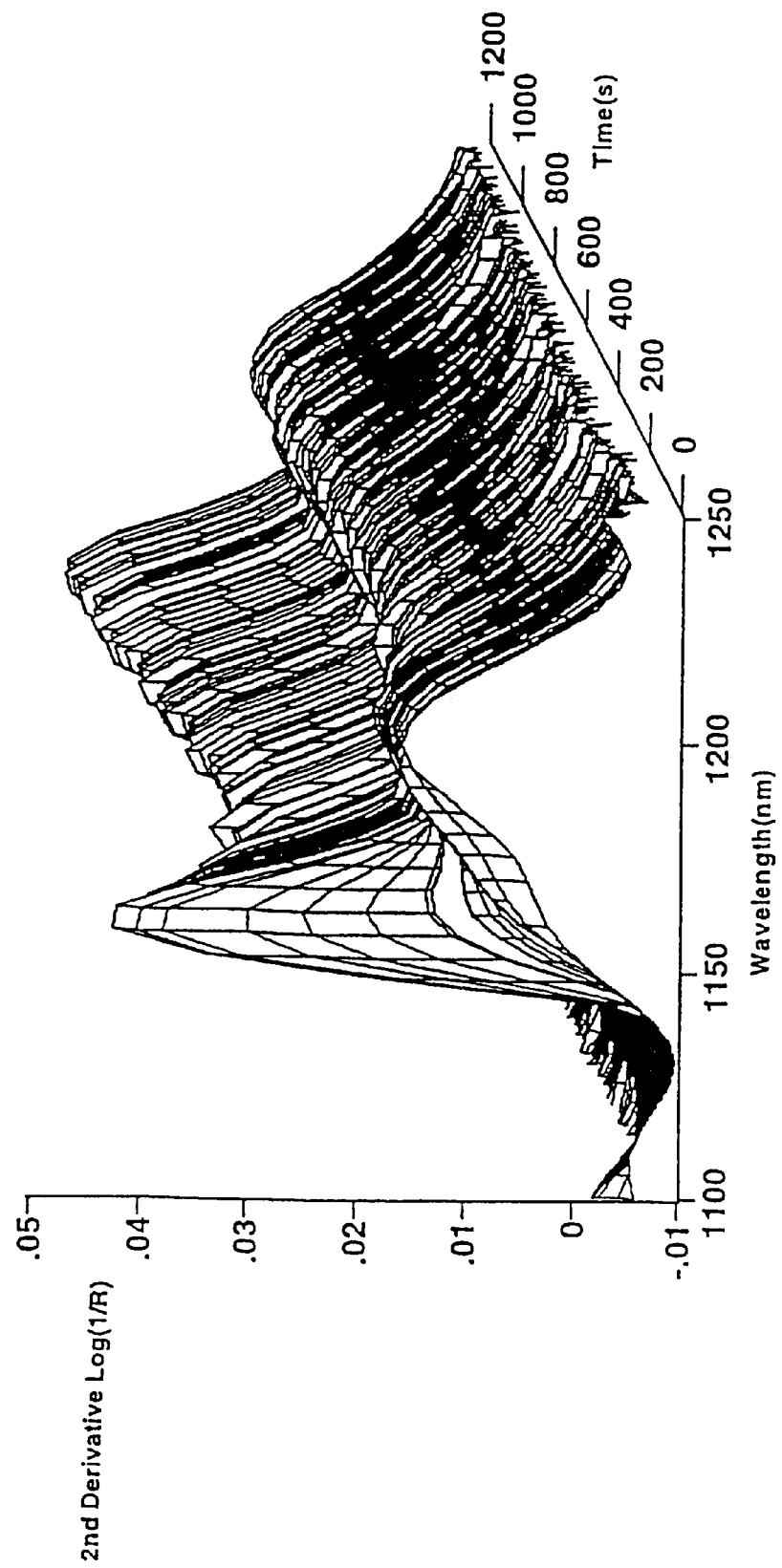
FIG. 2 shows inverted 2nd derivative spectra of an unyeasted dough mixed from Very Strong Flour in an Eberhardt mixer. Spectra recorded in real time with Perten DA-7000 spectrometer.
Figure 3:
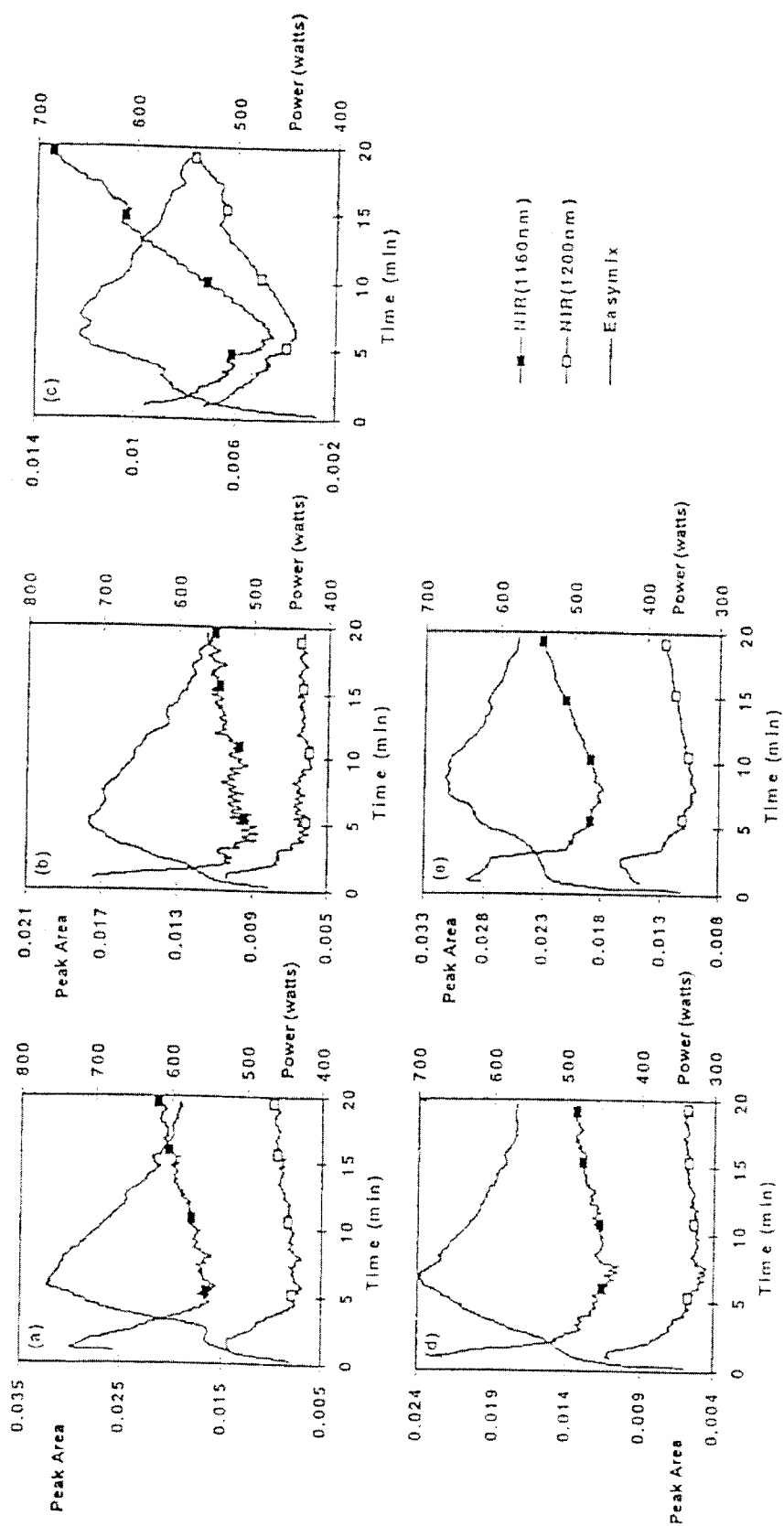
FIG. 3 shows mixing curves obtained for five systems using Eberhardt mixer and Perten DA-7000 spectrometer.(a) Very Strong Flour, unyeasted, (b) Very Strong Flour, yeasted, (c) Biscuit Flour, unyeasted, (d) strong flour, unyeasted and (e) Medium Flour, unyeasted.

Although spectral data were available in the range 400–1700 nm, it was decided that analysis would be restricted to the range 1100–1700 nm because this region contains the second overtones of absorbances to $CH_3$, $CH_2$, and CH and water. For example, $CH_2$ groups absorb at 1200 nm (Wheeler, O. H., Chemical Reviews, 1959 59 629–666). FIG. 2 shows a three-dimensional plot of the Perten spectra obtained from a dough mixed with Very Strong Flour. FIG. 3 shows the data recorded for doughs mixed using the Eberhardt mixer. In all five cases, the variation in the peak areas is consistent with the variation in power consumption recorded by Easymix. The four different flours could easily be differentiated by measuring the time for the NIR mixing curve to reach a minimum. In the case of the Eberhardt mixer, dough development is slow and the spectra are recorded at a point well away from the mixing spiral. Thus, the dough is not actually being mixed at the point where the spectra are recorded.

Interpretation of NIR spectra is difficult because of the broadness (in terms of bandwidth) and complexity of the absorbances. The spectra of the two principal constituents of dough, flour and water provide some insight into the source of the absorbances. The peak that occurs at 1160 nm in the dough spectrum is present in the spectrum of water, but is only seen as a shoulder in the second derivative spectrum of flour, whilst the absorbance seen at 1200 nm in dough appears to be exclusively due to the flour. As shown above, the absorbances in the region around 1200 nm are due to $C—H_x$ groups, where x is an integer from 1 to 3. Experiments using a starch water mix showed neither any variation in Log(1/R) in the NIR, nor any discernible variation in power consumption. Although this suggests that water absorption by starch does not contribute directly to the NIR mixing curve, contributions from a gluten-starch interaction cannot be ruled out. The shape of both the NIR mixing curves suggests that as mixing proceeds, less material which absorbs radiation at 1160 and 1200 nm is present until optimum dough development. As mixing proceeds past optimum, the absorbing species becomes more abundant. In the case of the absorbance at 1160 nm (due to water), any change in the environment of the water is likely to affect the fundamental frequency of the stretching and bending absorbances, which will affect the intensity of the combination band. Thus, as water is incorporated into the dough and hydrates the protein molecules, the intensity of the absorbance at 1160 nm decreases. Once past optimum, water is liberated from the dough and the absorbance increases; changes in the protein structure of the dough may also contribute to the variation observed in the NIR data.

EXAMPLE 3

Relationship between Mixer Speed, NIR Predicted Mixing Time and Mixograph Predicted Mixing Time A series of doughs were mixed using the Very Strong Flour as described in Table 1 and Example 1 on a 35 g Mixograph. A fibre optic interactance probe, available as a standard accessory for the Perten DA7000, was mounted transversely on the mixing bowl in order to obtain NIR spectra of the dough with minimal interference from the mixer head and pins. A shorted spectral acquisition time of 1.04 s was used because of the shorter mixing times achieved on the mixograph, compared to the mixers described in Example 2. Nine mixer speeds covering the range 0.998–2.048 revolutions per second(rps) were used, and two doughs were mixed at each speed. Mixograph resistance curves and the actual number of mixer revolutions were recorded at the same time.

Figure 5:
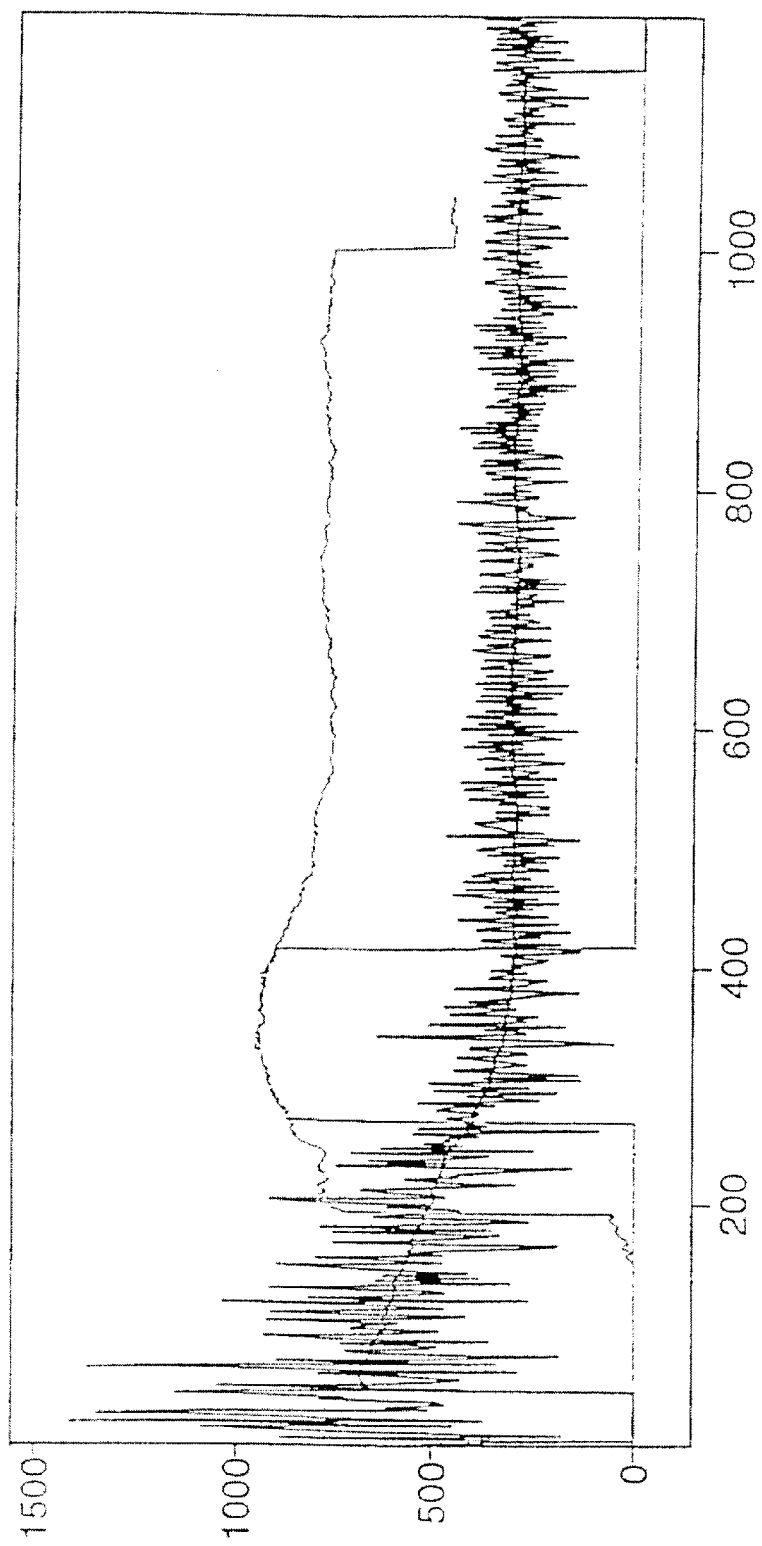
FIG. 5 shows a typical NIR mixing curve obtained from the 35 g Mixograph, with the smoothed curve and fitted gamma function and second derivative and fitted gamma function.
Figure 6:
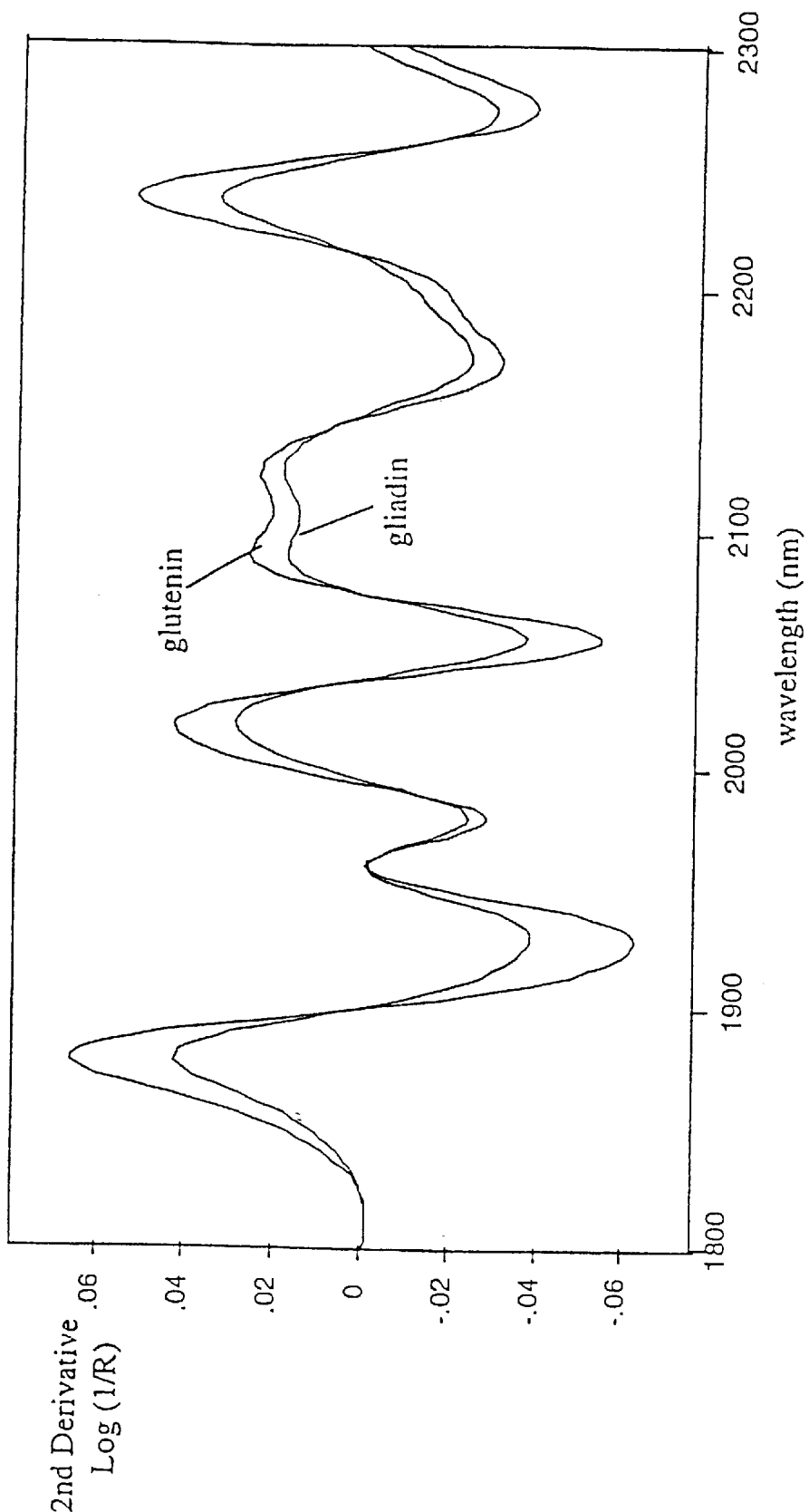
FIG. 6 shows second derivative spectra of gliadin and glutenin preparations from commercial bakers' flour from Queensland, Australia.

Data were processed using the methodology described in Example 2 above. The spectra were of slightly lower resolution due to the shorter acquisition time, so the 1200 nm band was not always clearly defined. Only the band at 1160 nm was used for the analysis. The resulting NIR mixing curves have a flatter profile than those recorded on the larger mixers (Example 2), so the second derivative of the smoothed curve was calculated and a gamma function fitted to identify the optimum mixing point, as shown in FIG. 5.

The results show that the NIR measurement consistently predicts a longer mixing time than the mixograph (significant at $p<0.05$) although it is not possible to say whether the difference is dependent on mixing speed. It has been reported that mixing beyond the time to peak resistance, as indicated by power consumption and mixograph, produces higher quality loaves of bread (Zounis, S. and Quail, K. J., "Predicting Test Bakery Requirements from Laboratory Mixing Tests", Journal of Cereal Science, 1997 25 185–196), and our results suggest that the NIR method might offer a better prediction of optimum dough development than power consumption or other physical measurements.

EXAMPLE 4

Figure 4:
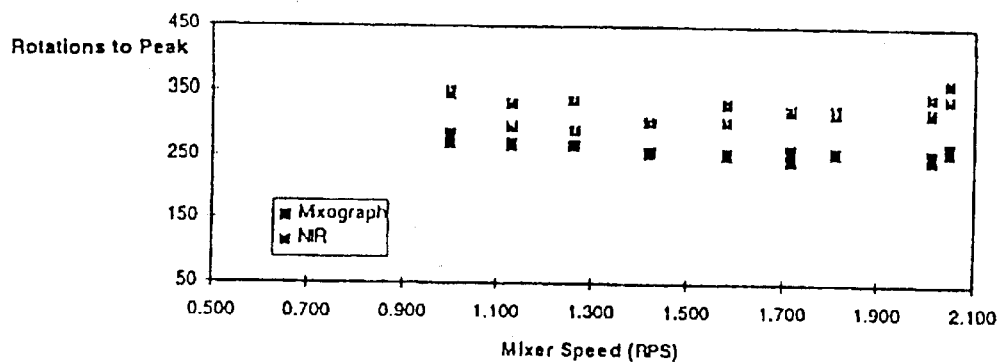
FIG. 4 shows the relationship between the mixing speed, NIR predicted mixing time and mixograph predicted mixing time for a strong flour mixed on a 35 g Mixograph. (a) Time to Peak vs Mixer Speed, (b) Number of Rotations to Peak vs Mixing Speed, (c) Rotation and Time Difference vs Mixing Speed and (d) Rotation and Time Percentage Difference vs Mixing Speed.
Figure 4:
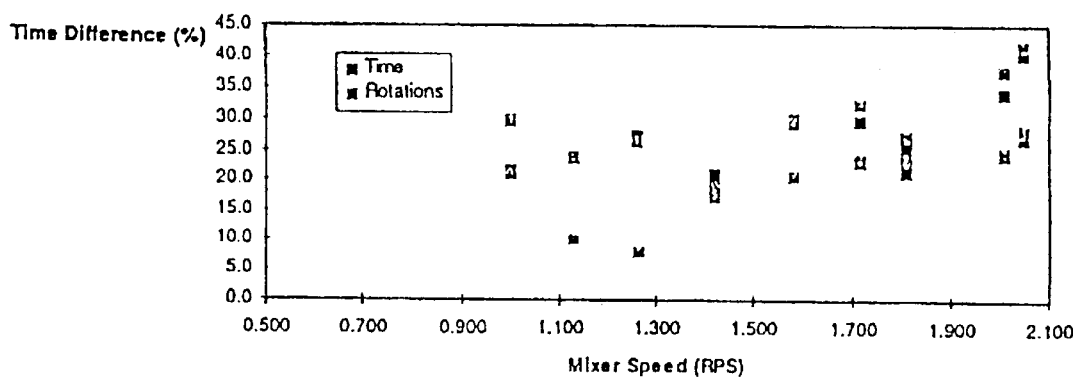
Figure 4:
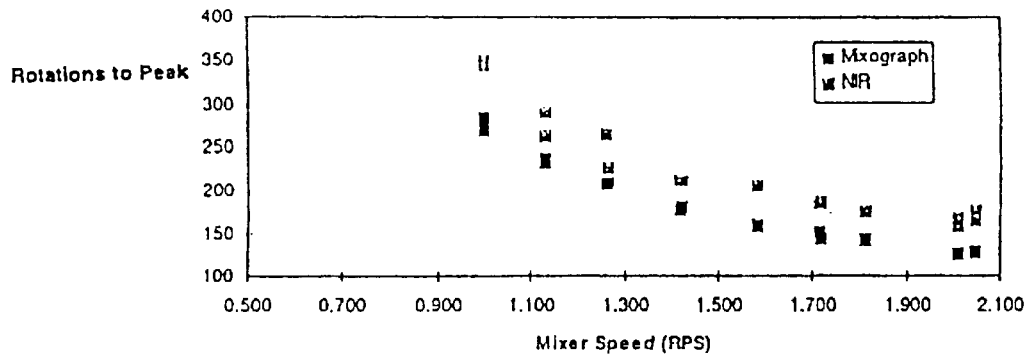
Figure 4:
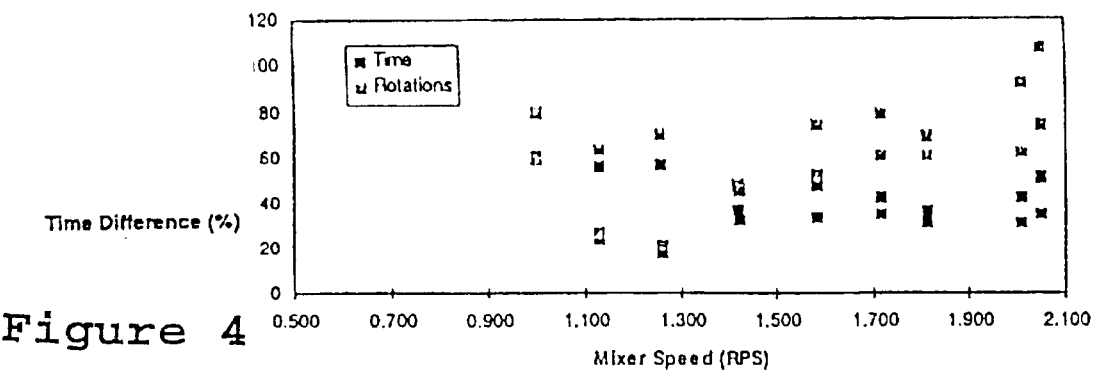

Analysis of the Glutenin and Gliadin Spectra and Content of Wheat Grain, Wholemeal, Flours and Products Purified preparations of gliadin and glutenin were isolated from flours of six wheats using an ethanol/dilute aqueous acid extraction process. After freeze-drying, the spectra of the isolated fractions provided reproducible and consistent differences. It is also well established that there is a relationship between glutenin content (or glutenin/gliadin ratio) and particular dough properties. The spectral differences between glutenin and gliadin in the second derivative spectrum, referred to above, are illustrated in FIG. 4. Since the ratio of gliadin and glutenin, and the content of glutenin in flours, provides a means for prediction of the dough processing (mixing and extension) properties (see papers by Preston and Tipples and by MacRitchie, referred to above) a method is provided for the objective prediction of dough properties through NIR analysis of grain, wholemeal, flour or wheat products.

EXAMPLE 5

Prediction of Time to Peak by NIR Analysis

Recent studies of the relationships between power consumption mixing curves and baking quality have suggested that the best baking quality is achieved when the dough is mixed beyond the time to peak (TTP). Typically, 20%–60% more mixing gives the best quality loaves in slower speed mixers(Quail, K. Australian Society of Baking. Proceedings of Fiftieth Anniversary Meeting 1996, 21–24). Using the NIR methods described herein, we have found that the time to peak predicted by NIR more closely agrees with the best baking quality for bread than does the time to peak predicted from power consumption curves (Easymix). This is particularly so for the Morton mixer. Typical results were as follows:

| Mixer | Easymix TTP (min) | NIR TTP (min) | Mixing time for best baking quality (min) |
| --- | --- | --- | --- |
| Eberhardt | 8.8 | 9.7 | 11.8 |
| Morton | 2.8 | 3.8 | 3.9 |

Thus, the NIR curves provide a better prediction of how much mixing is required for the best baking quality than Easymix analysis. Analyses of crumb strength, crumb extensibility and crumb softness also show that NIR is a better predictor of these quality characteristics than is Easymix analysis.

It will be recognised by those skilled in the art that numerous variations and modifications may be made to the invention as described above without departing from the spirit or scope of the invention as broadly described.

What is claimed is:

1. A method of measuring the change in constituents of a grain flour dough during mixing, comprising the steps of:
   (i) irradiating said grain dough with a range of wavelengths of light energy in the near infrared spectrum, said light energy being reflected from said grain dough;
   (ii) detecting the reflected light over said range of wavelengths by near infrared spectrophotometry at a plurality of time points throughout said mixing wherein a plurality of reflection spectra are obtained;
   (iii) calculating a value of the second derivative of said reflection spectra;
   (iv) inverting said second derivative of said reflection spectra and plotting the peak area with respect to time; and (v) determining the time at which the minimum peak area occurs.

2. The method according to claim 1, wherein the range of wavelengths of light energy in the near infrared spectrum is between about 800 nm to about 2500 nm.

3. The method according to claim 1, wherein the range of wavelengths of light energy in the near infrared spectrum is selected from the group consisting of 1160 nm, 1200 nm, 1430 nm, and 1940 nm.

4. The method according to claim 1, wherein the step of detecting the reflected light over said range of wavelengths is performed using a fast diode array or a fixed filter.

5. The method according to claim 1, wherein the step of detecting the reflected light over said range of wavelengths is performed for less than 30 seconds.

6. The method according to claim 1, wherein the step of detecting the reflected light over said range of wavelengths is performed for about 10 seconds.

7. The method according to claim 1, wherein the step of detecting the reflected light over said range of wavelengths is performed for about 1 second.

* * * * *